US009244039B2

(12) United States Patent
Balagurusamy

(10) Patent No.: US 9,244,039 B2
(45) Date of Patent: Jan. 26, 2016

(54) NANOPORE DEVICE WETTING

(71) Applicant: International Business Machines Corporation, Armonk, NY (US)

(72) Inventor: Venkat K. Balagurusamy, Suffern, NY (US)

(73) Assignee: International Business Machines Corporation, Armonk, NY (US)

( * ) Notice: Subject to any disclaimer, the term of this patent is extended or adjusted under 35 U.S.C. 154(b) by 267 days.

(21) Appl. No.: 13/951,109

(22) Filed: Jul. 25, 2013

(65) Prior Publication Data

US 2013/0334046 A1 Dec. 19, 2013

Related U.S. Application Data

(60) Division of application No. 13/535,882, filed on Jun. 28, 2012, now Pat. No. 8,702,944, which is a continuation of application No. 13/524,069, filed on Jun. 15, 2012, now abandoned.

(51) Int. Cl.
*G01N 27/447* (2006.01)
*G01N 33/487* (2006.01)
*B82Y 30/00* (2011.01)

(52) U.S. Cl.
CPC ........ *G01N 27/447* (2013.01); *G01N 33/48721* (2013.01); *B82Y 30/00* (2013.01)

(58) Field of Classification Search
CPC ............................ G01N 27/447; G01N 33/487
See application file for complete search history.

(56) References Cited

U.S. PATENT DOCUMENTS

| 6,407,435 | B1 | 6/2002 | Ma et al. | |
| 6,843,281 | B1 | 1/2005 | Barth et al. | |
| 7,001,501 | B2 * | 2/2006 | Spohr et al. | 205/640 |
| 7,846,738 | B2 * | 12/2010 | Golovchenko et al. | 436/86 |
| 2006/0105461 | A1 | 5/2006 | Tom-Moy et al. | |
| 2010/0295020 | A1 | 11/2010 | Barwicz et al. | |
| 2011/0053284 | A1 | 3/2011 | Meller et al. | |
| 2011/0279125 | A1 | 11/2011 | Bedell et al. | |
| 2012/0055236 | A1 | 3/2012 | Takulapalli | |
| 2014/0190833 | A1 * | 7/2014 | Lieber et al. | 204/627 |

OTHER PUBLICATIONS

Robertson et al. (PNAS, 2007).*
Meller et al. (PNAS, 2003).*
Maleki et al. (Nanotechnology, 20, 2009).*

(Continued)

*Primary Examiner* — Jennifer Dieterle
(74) *Attorney, Agent, or Firm* — Cantor Colburn LLP; Vazken Alexanian

(57) ABSTRACT

A method for wetting a nanopore device includes filling a first cavity of the nanopore device with a first buffer solution having a first potential hydrogen (pH) value, filling a second cavity of the nanopore device with a second buffer solution having a second pH value, wherein the nanopore device includes a transistor portion having a first surface, an opposing second surface, and an orifice communicative with the first surface and the second surface, the first surface partially defining the first cavity, the second surface partially defining the second cavity, applying a voltage in the nanopore device, and measuring a current in the nanopore device, the current having a current path partially defined by the first cavity, the second cavity, and the orifice.

10 Claims, 6 Drawing Sheets

(56) References Cited

OTHER PUBLICATIONS

M. Firnkes et al., "Electrically Facilitated Translocations of Proteins through Silicon Nitride Nanopores: Conjoint and Competitive Action of Diffusion, Electrophoresis, and Electroosmosis," Nano Lett., vol. 10, No. 6, 2010, pp. 2162-2167.

S. Harrer et al., "Electrochemical Protection of Thin Film Electrodes in Solid State Nanopores," Nanotechnology, vol. 22, 2011, 275304, 6 pages.

A. J. Storm et al., "Translocation of double-strand DNA through a silicon oxide nanopore," Phys. Rev. E, vol. 71, 2005, 051903, 10 pages.

L. Wang et al., "Nanofluidic Diode Generated by pH Gradient Inside Track-etched Conical Nanopore," 2010 3rd International Nanoelectronics Conference (INEC), Jan. 3-8, 2010, pp. 568-569.

R. Wei et al., "Fabrication of Metallized Nanopores in Silicon Nitride Membranes for Single-Molecule Sensing," Small, vol. 6, Issue 13, Jul. 5, 2010, published online Jun. 17, 2010, pp. 1406-1414.

\* cited by examiner

NANOPORE DEVICE WETTING

CROSS REFERENCE TO RELATED APPLICATIONS

The present application is a divisional of U.S. patent application Ser. No. 13/535,882, entitled "NANOPORE DEVICE WETTING", filed on Jun. 28, 2012, which is a continuation of U.S. patent application Ser. No. 13/524,069, entitled "NANOPORE DEVICE WETTING", filed on Jun. 15, 2012, the disclosures of which are incorporated by reference herein in their entirety.

FIELD OF INVENTION

The present invention relates generally to nanopore devices, and more specifically, to methods for fabricating and testing nanopore devices.

DESCRIPTION OF RELATED ART

Nanopore devices often include a substrate having at least a single orifice or "nanopore" and a pair of cavities disposed on opposing sides of the orifice. The cavities are operative to receive fluids that may include particles or structures such as, for example molecules that may be sensed by the nanopore devices as the molecules pass through the nanopore of the nanopore device. Typically, a voltage source and current sensing device are used to detect changes in the current that are affected by the molecules passing through the nanopore and can be used to detect the passage of single biomolecules like DNA, RNA and proteins, or nanoparticles through the nanopore sensing device. The changes in the current may be used to detect the presence of the molecules in the fluid.

BRIEF SUMMARY

According to one embodiment of the present invention, a method for wetting a nanopore device includes filling a first cavity of the nanopore device with a first buffer solution having a first potential hydrogen (pH) value, filling a second cavity of the nanopore device with a second buffer solution having a second pH value, wherein the nanopore device includes a transistor portion having a first surface, an opposing second surface, and an orifice communicative with the first surface and the second surface, the first surface partially defining the first cavity, the second surface partially defining the second cavity, applying a voltage in the nanopore device, and measuring a current in the nanopore device, the current having a current path partially defined by the first cavity, the second cavity, and the orifice.

According to another embodiment of the present invention, a method for wetting a nanopore device includes filling a first cavity of the nanopore device with a first buffer solution having a first potential hydrogen (pH) value, filling a second cavity of the nanopore device with the first buffer solution having the first pH value, wherein the nanopore device includes a transistor portion having a first surface, an opposing second surface, and an orifice communicative with the first surface and the second surface, the first surface partially defining the first cavity, the second surface partially defining the second cavity, applying a voltage in the nanopore device, measuring a current in the nanopore device, the current having a current path partially defined by the first cavity, the second cavity, and the orifice, flushing the first buffer solution having the first pH value from the second cavity and filling the second cavity with a second buffer solution having a second pH value, and measuring the current in the nanopore device.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Figure 1:
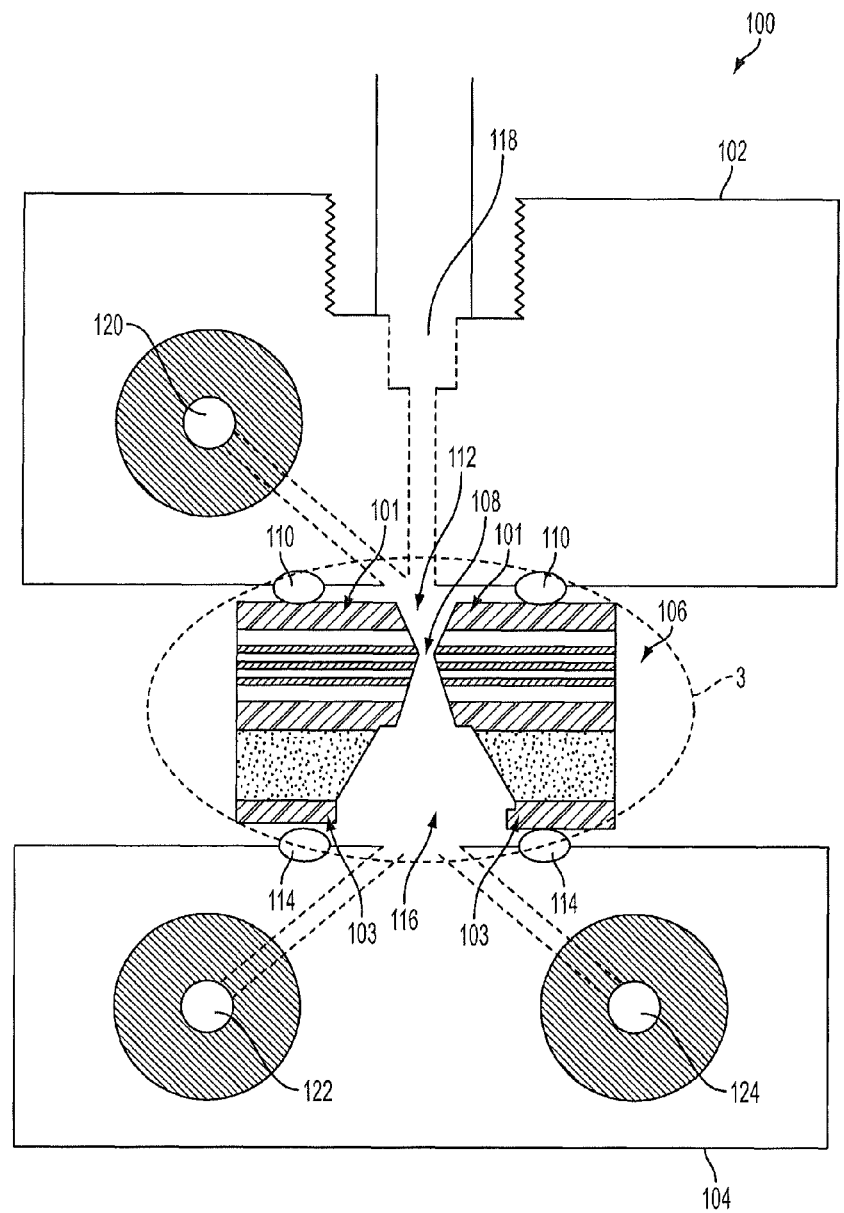
FIG. 1 illustrates a partially cut-away front view of an exemplary embodiment of a nanopore device.
Figure 2:
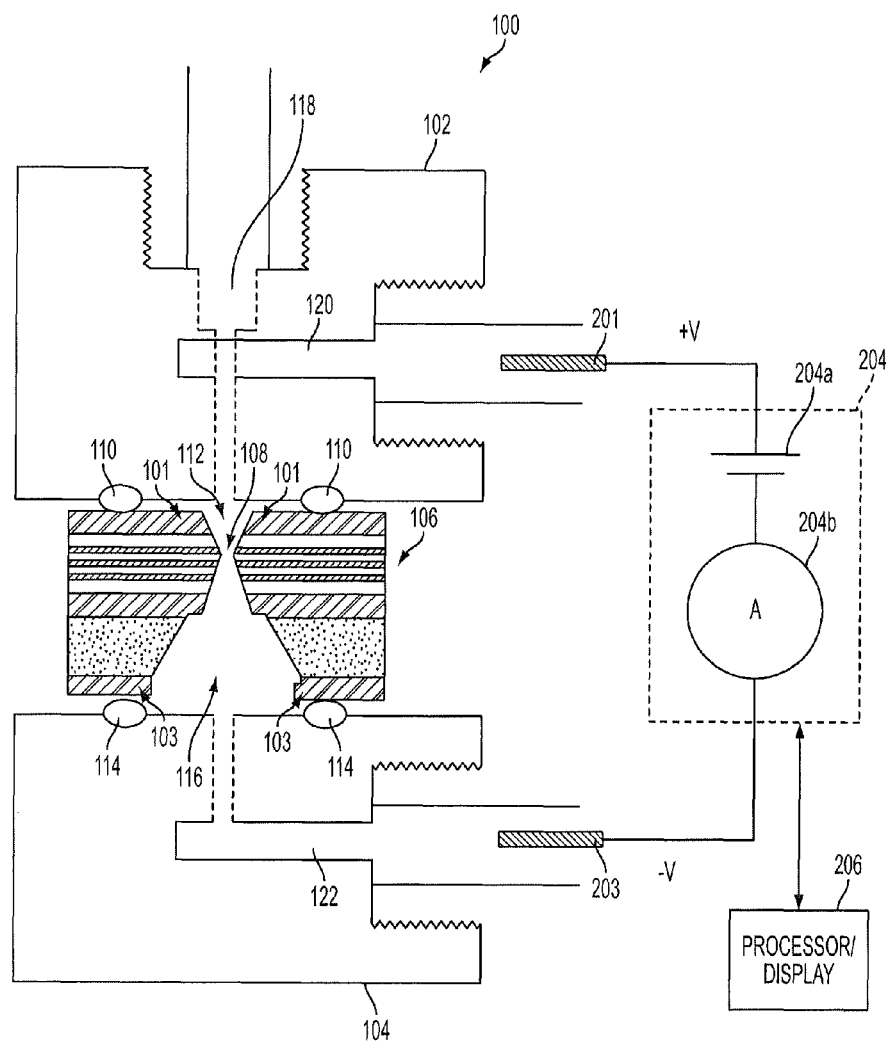
FIG. 2 illustrates a partially cut-away side view of the exemplary embodiment of a nanopore device of FIG. 1.

FIG. 1 and FIG. 2 illustrate a partially cut-away front and side view respectively of an exemplary embodiment of a nanopore device 100. Referring to FIG. 1, the nanopore device 100 defines a fluidic cell having a first substrate portion 102 and a second substrate portion 104. A DNA transistor device 106, hereafter "transistor device," is disposed between the first substrate portion 102 and the second substrate portion 104. The transistor device includes a first surface 101 and an opposing second surface 103. The transistor device 106 defines an orifice (i.e., nanopore) 108 that is communicative with the first surface 101 and the second surface 103. A first seal portion 110 is disposed between the first substrate portion 102 and the first surface. The transistor device 106, the first seal portion 110 and the first substrate portion 102 define a first cavity 112. A second seal portion 114 is disposed between the second surface 103 and the second substrate portion 104. The transistor device 106, the second seal portion 114, and the second substrate portion 104 define a second cavity 116. The first substrate portion 102 defines a first port 118 and a second port 120 that are communicative with the first cavity 112. The second substrate portion 104 defines a third port 122 and a fourth port 124 that are communicative with the second cavity 116.

Referring to FIG. 2, a voltage source 202a is arranged with terminals 201 and 203 disposed in the second port 120 and the third port 122. A current sensing device 202b is operative to detect changes in current between the terminals 201 and 203.

Figure 3:
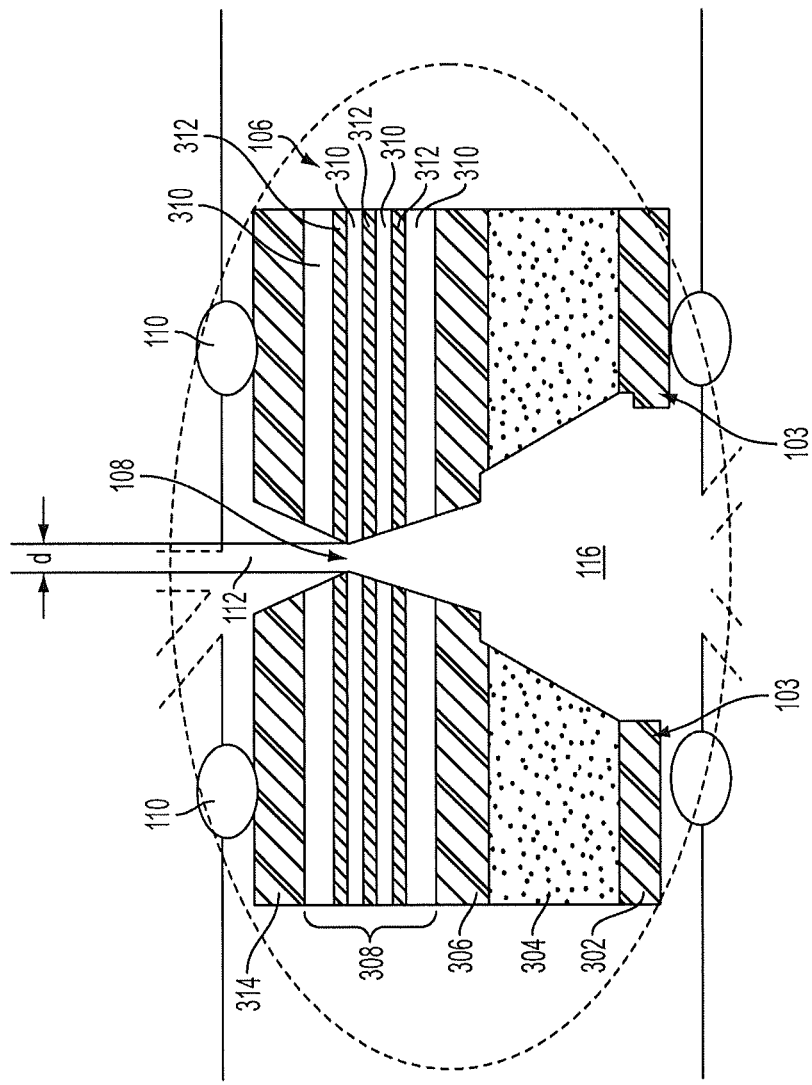
FIG. 3 illustrates a detailed view of the region 3 of FIG. 1.

FIG. 3 illustrates a detailed view of the region 3 (of FIG. 1). In this regard, the exemplary embodiment of the transistor device 106 includes a layer 302 of, for example, $Si_3N_x$ having a thickness of approximately 30 nm to 50 nm that defines the second surface 103. A layer 304 of, for example, Si is disposed on the layer 302 having a thickness of approximately 550 um. A layer 306 of, for example, $Si_3N_x$ having a thickness of approximately 30 nm to 50 nm is disposed on the layer 304.

A stack 308 that includes alternating layers of materials 310 and 312, such as, for example, TiN and SiO2 each having a thickness of approximately 5 nm is disposed on the layer 306. A layer 314 of, for example, $Si_3N_x$ having a thickness of approximately 30 nm to 50 nm that defines the first surface 101 is disposed on the stack 308. The orifice 108 has a diameter (d) of approximately 3 nm to 20 nm. The transistor device 106 may be fabricated using any suitable fabrication process that may include, for example, chemical vapor deposition (CVD), plasma enhanced chemical vapor deposition (PECVD), lithographic patterning and etching, and epitaxial growth processes. The transistor device 106 is but an exemplary embodiment. Other embodiments of the transistor device 106 or nanopore device may be used with the methods described below.

In operation, referring to FIG. 2, a fluid is used to fill the first cavity 112 and the second cavity 116. The fluid is introduced into the first cavity 112 via the first port 118 and the second port 120 and the second cavity 116 via the third port 122 and the fourth port 124. The fluid may be flushed from the first cavity 112 via the first port 118 and the second port 120, and the second cavity 116 via the third port 120 and the fourth port 124. However, in alternate embodiments, the roles of the ports may be reversed. The terminals 201 and 203 are communicative with the fluid such that an ionic current path through the fluid is defined by the second port 120, the first cavity 112, the orifice 108, the second cavity 116, and the third port 122. The ionic current in the current path is measured by the current sensing device 202b that may be connected to a processing and display device 206 that may include, for example, a computer processor and display operative to process the sensed current values and output a logical result to a user on the display. The ionic current is affected by the presence of molecules passing through the orifice 108. Thus, molecules in the fluid may be introduced into the first cavity 112 via the first port 118. The molecules affect the measured current as the molecules pass proximate to or through the orifice 108.

Prior to using the nanopore device 100 to measure the presence of molecules in the fluid, the nanopore device is prepared using an exemplary "wetting" method described below. The wetting method physically prepares the nanopore device 100 for operation, and includes a testing method that is used to determine whether the nanopore device 100 meets desired specifications and is calibrated to within desired thresholds.

Figure 4:
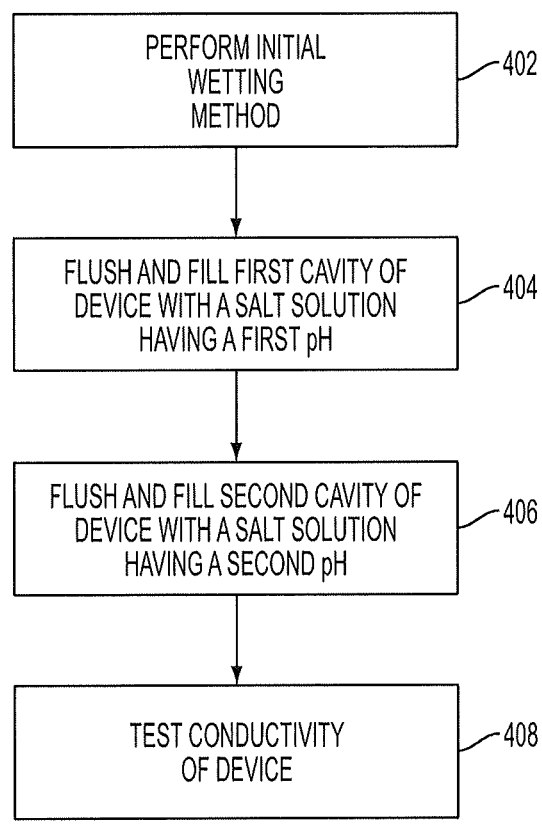
FIG. 4 illustrates a block diagram of an exemplary method for wetting the nanopore device of FIG. 1.

In this regard, FIG. 4 illustrates a block diagram of an exemplary method for wetting the nanopore device 100. In block 402, an initial wetting method is performed. The initial wetting method may include for example, flushing and filling one of the cavities 112 or 116 with isopropyl alcohol (IPA) and ensuring that there is no air gap or air bubble in the fluidic pathway. Waiting for a time period (e.g., at least five minutes) to allow vapor diffusion through the orifice 108 (of FIG. 1). Once the time period has expired, the remaining empty cavity 112 or 116 is flushed and filled with IPA. Another waiting period (e.g., at least five minutes) may be observed to complete the initial wetting method. Following the initial wetting method, the IPA is flushed from the cavities 112 and 116 and replaced with KCl buffer solutions having different potential hydrogen (pH) values in the respective cavities 112 and 116. For example, in block 404, the first cavity 112 is flushed and filled with a first KCl buffer solution having a first pH of approximately 7.5 to 8 with approximately 1 mM (milli Molar) concentration. In block 406, the second cavity 116 is flushed and filled with a second KCl buffer solution having a second pH of approximately 1.9 to 2.1 with approximately 1 mM concentration. In block 408, the conductivity of the nanopore device 100 is tested by applying a voltage and measuring the current in the fluid flow path for a time period (e.g., at least one hour) to determine whether the current increases and stabilizes during the time period.

Other initial wetting methods may include, for example, a plasma cleaning method, a piranha cleaning method that uses a concentrated sulphuric acid and hydrogen peroxide solution, or an electro wetting method that applies large direct current voltage pulses to the nanopore device 100.

If the measured current has stabilized to a desired or expected value, the KCl buffer solution in the second cavity 116 having the second pH may be flushed and replaced with a KCl buffer solution having a first pH of approximately 7.5-8 with approximately 1 mM concentration. The steps 404, 406 and 408 may be repeated in a similar manner with KCl buffer solutions having higher salt concentrations (e.g., 10 mM, 100 mM, and greater) if desired. Following a determination that the measured current in the nanopore device 100 meets designed specifications, the translocations of molecules introduced into a buffer solution in the first cavity 112 may be measured.

The difference between the pH values of the buffer solutions in the respective cavities during the wetting methods described herein affect properties of the materials in transistor device 106, and improve the conductivity that may be measured through the fluid in the nanopore device 100.

solution introduced into The exemplary method described above in FIG. 4 is not limited to the exemplary solutions described. For example, any salt concentration may be used, and any alternate pH values of the buffer solutions may be used. In the illustrated embodiment, the first cavity 112 receives a KCl buffer solution having a higher pH value than the KCl buffer the second cavity 116. However, alternate methods may, for example, introduce a KCl buffer solution into the first cavity 112 that has a lower pH value than a KCl buffer solution introduced into the second cavity 116. The pH values and the salt concentrations of the KCl buffer solutions used in the embodiments described above are chosen in part to accommodate a particular type of molecule (e.g., deoxyribonucleic acid (DNA)) that will be measured by the nanopore device 100. If another type of molecule will be measured by the nanopore device 100, alternate buffer solutions having, for example, different pH and salt concentrations may be used. For example, an alkali halide solution such as, LiCl, NaCl, CsCl and RbCl may be used.

Figure 5:
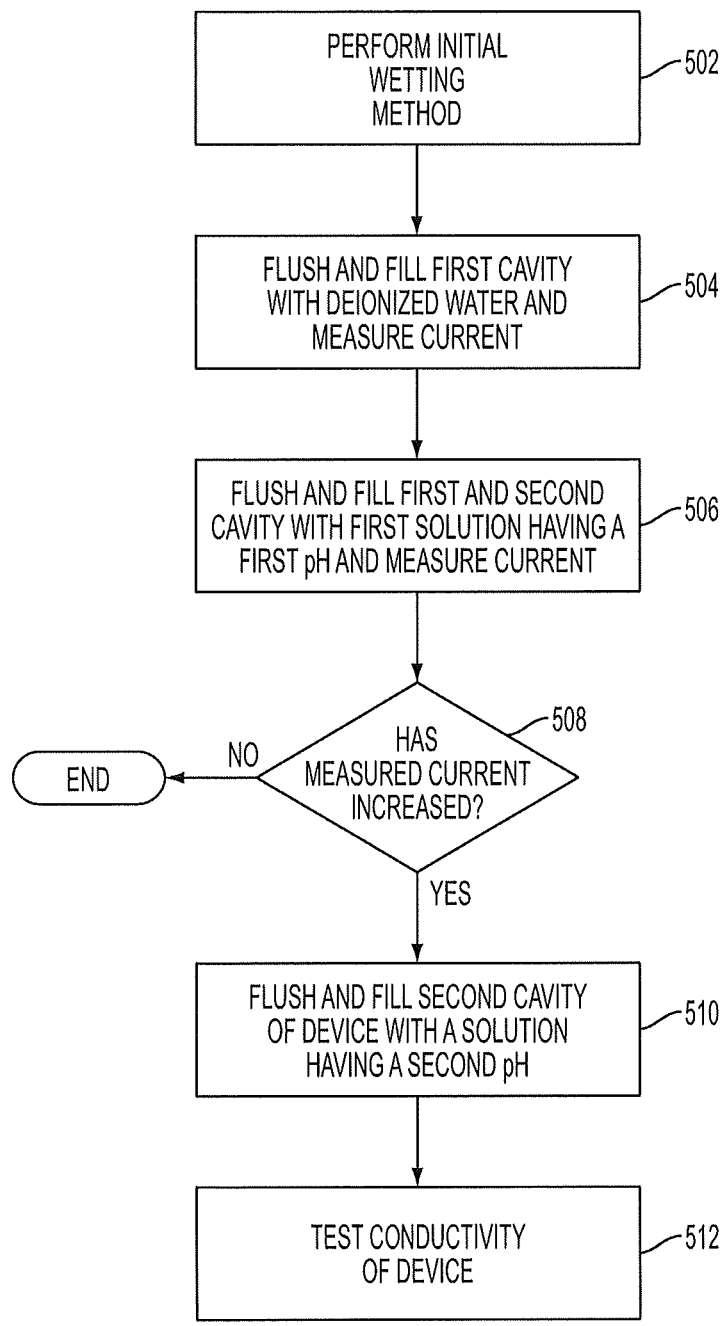
FIG. 5 illustrates an alternate wetting method for the nanopore device of FIG. 1.

FIG. 5 illustrates an alternate wetting method for the nanopore device 100 (of FIG. 1). In this regard, an initial wetting method with IPA is performed in block 502. The initial wetting method may be similar to the method described above in block 402. Following the wetting with IPA, one of the cavities 112 or 116 is flushed with deionized water having a pH of approximately 5.75. The current through the fluid in the nanopore device 100 may be measured to determine whether the current is greater than a desired threshold value. In block 506, the cavities 112 and 116 are flushed and filled with a KCl buffer solution having a first pH of approximately 7.5 to 8 with approximately 1 mM concentration, and the current is measured. The current measured in block 504 (where a cavity is filled with the deionized water) is compared to the current measured in the device in block 506 (where the cavities 112 and 116 are filled with the KCl buffer solution) to determine whether the measured current has increased following the introduction of the KCl buffer solution in block 508. If yes, the methods described in blocks 404, 406, and 408 (of FIG. 4) may be performed as shown in blocks 510, 512 respectively. In this regard, the second cavity 116 is flushed and filled with a solution having a second pH (e.g., 1.9-2.1 with approximately 1 mM concentration) in block 510. The conductivity of the device is tested in block 512. As discussed above in FIG. 4, the first and second cavities 112 and 116 may each be repeatedly flushed and filled with KCl solutions having dissimilar pH values and higher salt concentrations followed by testing the conductivity of the nanopore device 100 if desired. When the measured conductivity of the device meets or exceeds a desired threshold value, the device may be used to measure translocations of molecules in the solution if desired. In an exemplary embodiment, if the measured current has not increased following the introduction of the KCl buffer solution in block 508, the first and second cavities 112 and 116 may each be flushed with deionized water and kept filled with deionized water for a period of successive days. Following the period of days, the first and second cavities 112 and 116 may each be filled with a KCl solution, which may then exhibit an increase in the measured conductivity of the device.

Figure 6:
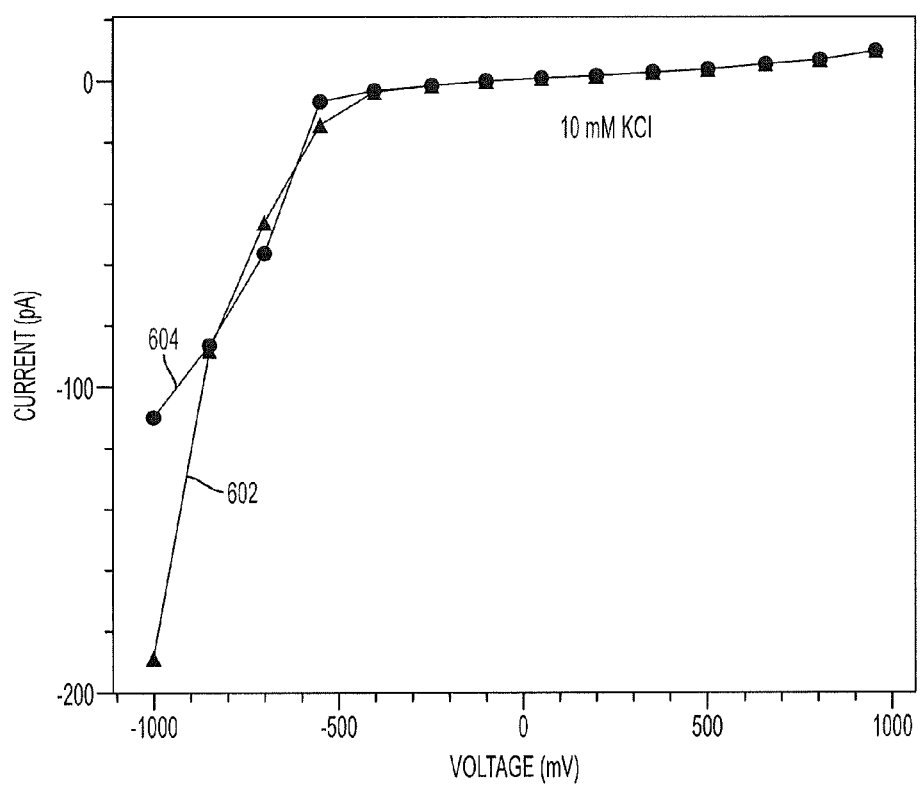
FIG. 6 illustrates a graph that shows comparative test results of measured currents in nanopore devices.

FIG. 6 illustrates a graph that shows comparative test results of measured currents in a nanopore device 100 (of FIG. 1). The line 602 illustrates the measured current over a range of voltages that was wet using the methods described above where the first cavity 112 of the nanopore device 100 was filled with a 10 mM KCl solution having a pH value of approximately 8, and the second cavity 116 of the nanopore device 100 was filled with a 10 mM KCl solution having a pH value of approximately 1.9. The line 604 illustrates the measured current over a range of voltages of a nanopore device 100 that was wet using, a 10 mM KCl solution having a pH value of approximately 8 in both the first cavity 112 and the second cavity 116. In this regard, the graph illustrates the greater measured current of the nanopore device 100 that was wet using buffer solutions having dissimilar pH values in the respective cavities as compared to the nanopore device that was wet using a uniform buffer solution in both cavities.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method for wetting a nanopore device, the method comprising:
    filling a first cavity of the nanopore device with a first buffer solution having a first potential hydrogen (pH) value;
    filling a second cavity of the nanopore device with the first buffer solution having the first pH value, wherein the nanopore device includes a transistor portion having a first surface, an opposing second surface, and an orifice communicative with the first surface and the second surface, the first surface partially defining the first cavity, the second surface partially defining the second cavity;
    measuring a first current in the nanopore device in response to applying a first voltage in the nanopore device, the first current having a current path partially defined by the first cavity, the second cavity, and the orifice;
    flushing the first buffer solution having the first pH value from the second cavity and filling the second cavity with a second buffer solution having a second pH value of 1.9 to 2.1, wherein the second pH value is different from the first pH value; and
    measuring a second current in the nanopore device in response to applying a second voltage in the nanopore device.

2. The method of claim 1, wherein the first pH value is greater than the second pH value.

3. The method of claim 1, wherein the second pH value is greater than the first pH value.

4. The method of claim 1, wherein the first buffer solution is a KCl solution.

5. The method of claim 1, wherein the second buffer solution is a KCl solution.

6. The method of claim 1, wherein prior to filling the first cavity of the nanopore device with the first buffer solution, the method includes performing an initial wetting method.

7. The method of claim 6, wherein the initial wetting method includes:
    filling the first cavity with isopropyl alcohol (IPA); and
    filling the second cavity with IPA.

8. The method of claim 6, wherein the initial wetting method includes:
    filling the first cavity with deionized water;
    filling the second cavity with deionized water;
    applying a voltage in the nanopore device; and
    measuring the current in the nanopore device.

9. The method of claim 1, wherein the nanopore device includes a first port communicative with the first cavity and a second port communicative with the first cavity, wherein the filling the first cavity of the nanopore device is performed by introducing the first buffer solution into the first cavity through the first port.

10. The method of claim 1, wherein the nanopore device includes a third port communicative with the second cavity and a fourth port communicative with the second cavity, wherein the filling the second cavity of the nanopore device is performed by introducing the second buffer solution into the second cavity through the third port.

* * * * *